US012751967B2

(12) United States Patent
Jerusik et al.

(10) Patent No.: US 12,751,967 B2
(45) Date of Patent: Oct. 6, 2026

(54) COMPOSITIONS, METHODS, SYSTEMS AND KITS FOR THE TREATMENT OF NOSEBLEEDS

(71) Applicant: ADVANCED RX, Fort Washington, PA (US)

(72) Inventors: Jason Sassan Jerusik, Plymouth Meeting, PA (US); Kyle Stephen Salata, Flourtown, PA (US)

(73) Assignee: ADVANCED RX, Fort Washington, PA (US)

( * ) Notice: Subject to any disclaimer, the term of this patent is extended or adjusted under 35 U.S.C. 154(b) by 402 days.

(21) Appl. No.: 17/946,556

(22) Filed: Sep. 16, 2022

(65) Prior Publication Data

US 2023/0090238 A1 Mar. 23, 2023

Related U.S. Application Data

(60) Provisional application No. 63/245,220, filed on Sep. 17, 2021.

(51) Int. Cl.
*A61K 31/765* (2006.01)
*A61K 9/00* (2006.01)
*A61K 9/06* (2006.01)

(52) U.S. Cl.
CPC .......... *A61K 31/765* (2013.01); *A61K 9/0043* (2013.01); *A61K 9/06* (2013.01)

(58) Field of Classification Search
CPC ...... A61K 31/765; A61K 9/0043; A61K 9/06; A61K 47/02; A61K 47/10; A61K 47/186; A61P 7/00
See application file for complete search history.

(56) References Cited

U.S. PATENT DOCUMENTS 5,885,587 A * 3/1999 Botknecht ............... A61P 31/04 530/412
2006/0034947 A1 * 2/2006 Burr ..................... A61K 36/752 514/738
2008/0281197 A1 11/2008 Wiley et al.
2009/0162438 A1 6/2009 Fuler et al.
2011/0008266 A1 1/2011 Tamarkin et al.
2015/0030684 A1 1/2015 Pomrinken et al.

OTHER PUBLICATIONS

Peterson, Epistaxis, JAMA p. 1006, Sep. 2020.*
Bermudez, Thermosen. Poloxamer, J. of Pharm. and Pharma. p. 109, Sep. 2011.*
International Search Report and Written Opinion (Forms PCT/ISA/210 and PCT/ISA/237) issued on Feb. 7, 2023, by the International Searching Authority in corresponding International Application No. PCT/US22/43782. (16 pages).
Bhandwalkar, Mandar J., et al., “Thermoreversible Nasal In situ Gel of Venlafaxine Hydrochloride:Formulation, Characterization, and Pharmacodynamic Evaluation” AAPS PharmSciTech, Mar. 2013, pp. 101-110, vol. 14, No. 1. (p. 10).
Li, Cong, et al. “Preparation of levofloxacin thermo-sensitive gel and clinical application in the treatment of suppurative otitis media”, Acta Oto-Laryngologica., 2014 (month unknown), pp. 468-474, vol. 134, Informa Healthcare. (7 pages).
Mfoafo, Kwadwo, et al. “Contemporary applications of thermogelling PEO-PPO-PEO triblock copolymers”, Journal of Drug Delivery Science and Technology, Feb. 2022, pp. 1-17, vol. 70, Elsevier B.V. (17 pages).
Shelke, Santosh, et al. “Formulation and evaluation of thermoreversible mucoadhesive in-situ gel for intranasal delivery of naratriptan hydrochloride”, Journal of Drug Delivery Science and Technology, Aug. 2015, pp. 238-244, vol. 29, Elsevier B.V. (7 pages).
Yong, Chul Soon, et al. “Effect of sodium chloride on the gelation temperature, gel strength and bioadhesive force of poloxamer gels containing diclofenac sodium”, International Journal of Pharmaceutics, Jul. 2001, pp. 195-205, vol. 226, Elsevier Science B.V. (11 pages).

* cited by examiner

*Primary Examiner* — David J Blanchard
*Assistant Examiner* — Thurman Wheeler
(74) *Attorney, Agent, or Firm* — Elmore Patent Law Group, P.C.; Carolyn S. Elmore

(57) ABSTRACT

A floor panel assembly including a first and a second panel. A first edge portion of the first panel includes an upwardly extending locking element and a second edge portion of the second panel includes a downwardly open locking groove configured to cooperate with the locking element for horizontally locking. The floor panel assembly includes a connecting device configured to be at least partially arranged in the locking groove in a locked state of the first and second edge portions. An outer portion of a strip of the first panel includes a cavity extending below an upper surface of the locking element. An upper section of the connecting device includes a projection extending from a body portion, wherein the projection is arranged in the cavity in the locked state.

15 Claims, No Drawings

COMPOSITIONS, METHODS, SYSTEMS AND KITS FOR THE TREATMENT OF NOSEBLEEDS

GOVERNMENT SPONSORSHIP

The present disclosure was funded by the STAR Grant from the Washington University Institute of Clinical and Translational Sciences (ICTS) and supported by the National Center for Advancing Translational Sciences of the National Institutes of Health under Award Number TL1TR002344 (AMP). The government has certain rights in the invention.

TECHNICAL FIELD

The present disclosure relates to the use of compositions comprising thermoreversible poloxamer gels capable of remaining as a solution at room temperature and transitioning into a gel once exposed to physiological temperatures within the nose of a subject as a method of treatment for nosebleeds. The disclosed compositions may also be incorporated into systems and kits to treatment nosebleeds.

BACKGROUND

Poloxamers include groups of copolymers comprising ethylene oxide (EO) and/or propylene oxide (PO) blocks arranged in a triblock structure. Poloxamers cover a large range of liquids, pastes and solids. They may be synthesized by sequential polymerization of PO and EO monomers.

Poloxamer gels were first introduced in the late 1950's and have been used in many different pharmaceutical formulations, most of which involve the encapsulation or co-delivery of pharmaceutical agents, radiotrackers, biomarkers or cell signaling molecules, in addition to other agents.

Typically, when poloxamer gels are exposed to a cooler temperature, such as in a refrigerator or potentially at room temperature, the poloxamer may possess a thick liquid consistency or may remain a liquid. However, when the poloxamer is exposed to increasing temperatures, the poloxamer begins to solidify into a gel. When the poloxamer exists as a gel, its mucoadhesive properties increase, thus allowing it to adhere to the mucosa membranes within the body for an extended period of time. For this reason, poloxamer gels have been used in the application of medicated ear drops, medicated ophthalmic drops, and medicated suppositories. Various medications including venlafaxine for depression, naratriptan and sumatriptan for migraines, antibiotics, corticosteroids and anti-inflammatories have been studied in formulations comprising poloxamer gels.

Poloxamer 407 is a known ingredient in poloxamers gels and has been presented as a drug carrier ingredient for different types of preparations (e.g., IV, inhalation, oral solution, suspension, ophthalmic or topical formulations) by the FDA. Indeed, poloxamer 407 has been shown to be effective as a drug carrier for a wide array of pharmaceutical agents. For example, poloxamer 407 has been shown to successfully treat suppurative otitis media (SOM) through the well-controlled release of levofloxacin targeted against inflammation (Li et al., Acta Oto-Laryngologica. 134: 468-474 (2014)). Furthermore, there is an ongoing clinical study evaluating the effectiveness of a poloxamer gel containing poloxamer 407 gel with either antibiotics, corticosteroids or both to improve the recovery time of chronic sinusitis patients that have undergone a balloon sinuplasty surgery (LifeBridge Health, Gel-Sinuplasty for Chronic Rhinosinusitis With and Without Nasal Polyposis, NCT03472144).

Poloxamer 407 may also be combined with other formulating agents to improve the delivery of pharmaceutical agents to subjects in need thereof. Poloxamer gels have been formulated by using poloxamer 407 and carbopol 934, a carbomer, to improve the bioavailability of naratriptan hydrochloride, an approved drug molecule used to treat migraine headaches (Shelke et al. *Journal of Drug Delivery Science and Technology.* 29, 238-244 (2015)). Poloxamer 407 has also been combined with carbopol 934 to improve the delivery and bioavailability of sumatriptan, another drug used to treat migraines and cluster headaches. In addition to improving the delivery of drugs to treat migraines or headaches, combinations of poloxamer 407 and carbopol 934 have also been discovered to improve the delivery of antidepressants, such as venlafaxine hydrochloride (Bhandwalkar et al. *AAPS PharmSciTech.* 14:1 (2013)).

Poloxamer 407 can also be combined with other poloxamers to improve the overall delivery of pharmaceutical agents. Combinations of poloxamer 407 and poloxamer 188 have been implemented in successful drug delivery formulations. For example, a composition containing a combination of poloxamer 407 and poloxamer 188 with the anti-inflammatory drug diclofenac sodium has been found to possess an improved drug delivery when inserted into the rectums of rabbits (Yong et al., *Int. J. Pharm.* 226, 195-205 (2001)).

SUMMARY

Though poloxamer gels have been studied and implemented in studies aimed at improving the delivery of pharmaceutical agents, these gels have not been explored as a treatment method of other ailments, such as chronic nosebleeds. Subjects or patients experiencing chronic nosebleeds may suffer from being exposed to a dry environment that causes the mucosa in the nose to dry-out, thus leading to constant picking of the nose and possible rupture of blood vessels. Chronic nosebleeds can also occur from constant exposure to allergens which may cause the nose to over secrete mucus. The over secretion of mucus may cause a subject or patient to blow their nose too often, which can also lead to the rupturing of blood vessels in the nose. Some subjects or patients may also possess structural problems or defects in their noses which can promote the onset of chronic nosebleeds. Patients suffering from Hereditary Hemorrhagic Telangiectasia (HHT), an inherited disorder that causes abnormal connections, called arteriovenous malformations (AVMs), to develop between arteries and veins is an example of a condition that can lead to chronic nosebleeds.

Hence, an objective of the embodiments described in the present disclosure is to create a composition comprising a poloxamer gel formulation that can be used in the treatment of chronic nosebleeds in a subject in need thereof.

Embodiments of the present disclosure include a composition comprising a poloxamer gel, wherein the poloxamer gel is a combination of poloxamer 407 and poloxamer 188, wherein the composition further comprises preserved water and wherein the composition does not contain pharmaceutical agents and radioactive compounds.

The composition may include an amount of poloxamer 407 that contributes 0.1% to 40% towards the total weight of the composition and an amount of poloxamer 188 that contributes 0.1% to 40% towards the total weight of the composition.

The composition may further include NaCl. NaCl may be present in an amount that contributes 0.1% to 50% towards the total weight of the composition. NaCl may be present in an amount that contributes 0.5% to 2.0% towards the total weight of the composition.

The amount of poloxamer 407 may contribute 10% to 20% towards the total weight of the composition and the amount of poloxamer 188 may contribute 10% to 20% towards the total weight of the composition.

The composition may possess a pH range from 4.5 to 8.0.

The composition may be a soft gel at temperatures ranging from 25.5° C. to 28.9° C. and a solid at temperatures ranging from 30° C. to 36° C.

The composition may further comprise an excipient selected from the group comprising moisturizers or cleansers.

The moisturizer(s) may contribute 0.1% to 50% towards the total weight of the composition and the cleansers contribute 0.1% to 80% towards the total weight of the composition.

The moisturizer(s) may be selected from aloe vera, propylene glycol, polyethylene glycol, potassium salts or combinations thereof and the cleanser may be xylitol.

Embodiments of the present disclosure further include a composition comprising a poloxamer gel, wherein the poloxamer gel is a combination of poloxamer 407 and poloxamer 188; and preserved water. The composition may be formed from poloxamer gel components having a mean size of at most 0.5 mm; and the composition may be a gel at temperatures ranging from 25.5° C. to 28.9° C. and a solid at temperatures ranging from 30° C. to 36° C.

The composition may further include NaCl. NaCl may be present in an amount that contributes 0.1% to 50% towards the total weight of the composition.

The composition may include: 0.1-50 wt % of poloxamer 407; and 0.1-50 wt % of poloxamer 188.

The composition may include: 10-25 wt % of poloxamer 407; 10-25 wt % of poloxamer 188; and 0.6-1.1 wt % NaCl.

Embodiments of the present disclosure also include a method for treating nosebleeds in a subject in need thereof comprising administering a poloxamer gel composition, wherein the poloxamer gel composition comprises poloxamer 407 and poloxamer 188, wherein the amount of poloxamer 407 contributes 0.1% to 50% towards the total weight of the composition and the amount of poloxamer 188 contributes 0.1% to 50% towards the total weight of the composition; wherein the poloxamer gel composition further includes water, such as preserved water; wherein the poloxamer gel composition is a solid at temperatures ranging from 30° C. to 36° C.; wherein the poloxamer gel composition possesses a pH between 4.5 and 8.0; wherein the composition is administered into the nasal cavity of the subject and wherein the method further includes reducing the number of nosebleeds per day in the subject in need thereof.

The composition may further include NaCl in an amount that contributes 0.1% to 50% towards the overall weight of the composition.

The composition may be administered once or twice a day.

The method may further include reducing the severity of nose bleeds in the subject in need thereof.

DETAILED DESCRIPTION

As used herein the term "comprising" or "comprises" as used in reference to compositions, methods, etc. refers to component(s) or method steps that are present in the method or composition, yet allows for the composition, method, etc. to also include unspecified elements.

As used herein the term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment. Such elements may be excipients which improve the formulation of the present compositions, such as moisturizers, cleansers or salts that do not act as pharmaceutical agents. Elements or components that may materially affect the basic and novel functions of the present compositions, can be pharmaceutical agents. These pharmaceutical agents can be cell signaling molecules, antibiotics, antifungals, antivirals, anti-inflammatories, corticosteroids, drug-approved small molecules or other compounds used to alleviate or treat a disease or infection. Salts possessing a substantive therapeutic effect, such as diclofenac sodium, are also considered to be a pharmaceutical agent and would be considered pharmaceutical agents.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the terms "prevent" or "prevention" and other derivatives of the words, when used in reference to nosebleeds, refer to a reduced likelihood of nosebleeds in an individual receiving a given treatment relative to that of a similar individual at risk for nosebleeds but not receiving that treatment. As such, the terms "prevent" and "prevention" encompass a treatment that results in a lesser degree of nosebleeds than would be otherwise expected for a given individual. Efficacy for prevention of nosebleeds can be established through controlled studies, e.g., in which a subject is administered a treatment (e.g., a nasal treatment) and another subject is administered a placebo. Under these circumstances, if the subject treated with the nasal treatment develops less nosebleeds over time, such as within 1 to 2 days or within a week, relative to the subject receiving the placebo, e.g., at least 5% less, at least 10% less, at least 15% less, at least 20% less, at least 25% less, at least 30% less, at least 35% less, at least 40% less, at least 45% less, at least 50% less or beyond, the treatment is effective for the prevention of nosebleeds.

As used herein, the terms "treat," "treatment," or "treating" refer to therapeutic treatments, wherein the object is to reverse, alleviate, ameliorate, inhibit, slow down or stop the progression or severity of a disease or condition, e.g., nosebleeds. The term "treating" includes reducing or alleviating at least one adverse effect or symptom of a disease or condition, e.g., nosebleeds. Treatment is generally "effective" if one or more symptoms are reduced. Alternatively, treatment is "effective" if the progression of a disease or condition is reduced or halted. That is, "treatment" includes not just the improvement of symptoms, but also a cessation of, or at least slowing of, progress or worsening of symptoms compared to what would be expected in the absence of treatment. Beneficial or desired clinical results include, but are not limited to, alleviation of one or more symptom(s), diminishment of extent of condition, stabilized (i.e., not worsening) state of condition, delay or slowing of disease progression, amelioration or palliation of the disease state, remission (whether partial or total), and/or decreased mortality. For example, treatment is considered effective if the extent or amount of nosebleeds is reduced, or the development of nosebleeds is slowed or halted. The term "treatment" of a condition also includes providing relief from the symptoms or side-effects of the condition (including palliative treatment).

As used herein, the term "subject" refers to a mammal in need of a therapeutic treatment for nosebleeds. In embodiments, the subject is a human.

As used herein, the term "pharmaceutical agents" refers to any molecule (e.g., protein (e.g., an antibody, antigen-binding fragment of an antibody, or a derivative or conjugate thereof), nucleic acid, lipid, carbohydrate, or small molecule (e.g., inorganic, organic, or mixed inorganic-organic molecule), or combination thereof) that is administered to a subject in order to treat or alleviate an infection or disease. Some examples of pharmaceutical agents are cell signaling molecules, antibiotics, antifungals, antivirals, anti-inflammatories, corticosteroids, drug-approved small molecules or other compounds used to alleviate or treat a disease or infection.

As used herein, the term "excipients" refers to compounds that may be included within the compositions of the present application. Some examples of excipients are moisturizers, cleansers or salts that do not act as pharmaceutical agents.

As used herein, the term "solid" refers to a gel that possesses a hard or tough consistency which is capable of solidifying and remaining within a nasal cavity after application. A gel composition may be characterized as a solid when one of its physical properties is effectively higher when exposed to higher temperatures as compared to exposure of the gel at lower temperatures. Some of the physical properties that can be measured to determine if a gel is "solid" may include, but are not limited to, viscosity, flow rate, gel strength, mechanical modulus, flexural modulus, elastic modulus, stiffness and/or tensile strength.

For example, a solid may be a highly viscous fluid which may have a viscosity of greater than 200,000 cP, such as greater than 500,000 cP, such as greater than 1,000,000 cP, such as greater than 5,000,000 cP. For example, the solid may have, effectively, an unmeasurable viscosity.

As used herein, the term "soft gel" refers to a gel that possesses a soft or weak consistency which is typically too fluid for remaining within a nasal cavity after application. A gel composition may be characterized as a soft gel when one of its physical properties is effectively lower when exposed to low temperatures as compared to exposure of the gel at higher temperatures. Some of the physical properties that can be measured to determine if a gel is a soft gel may include, but are not limited to, viscosity, flow rate, gel strength, mechanical modulus, flexural modulus, elastic modulus, stiffness and/or tensile strength.

For example, a soft gel may have a viscosity of less than about 10,000 cP, such as less than 1,000 cP, such as less than 300 cP, such as less than 280 cP, such as less than 260 cP.

As used herein, the term "liquid" refers to a gel composition that is free flowing and has a consistency similar to water or oil. A gel composition may be characterized as a liquid when it possesses a viscosity of less than about 260 cP, such as 200 cP, such as less than 150 cP, such as less than 100 cp, such as less than 50 cP or possesses a viscosity around 1 cP.

Viscosity may be measured using methods conventionally employed by those of ordinary skill. One method for measuring viscosity may comprise the use of a small sample adapter, a viscometer and a water bath. The viscosity of a poloxamer gel composition may be measured at temperatures ranging from 2° C. to 25° C., 25.5° C. to 28.9° C. or 30° C. to 36° C.

Poloxamer gels comprising poloxamer 407 in combination with poloxamer 188 are effective drug delivery systems; however, prior to present disclosure, they have yet to be evaluated as treatments for nosebleeds. Hence, the present disclosure relates to compositions of poloxamers that can be used in treatments, systems and kits to prevent, treat or alleviate the symptoms and occurrences of nosebleeds.

The compositions of the present disclosure comprise a poloxamer gel, wherein the poloxamer gel is a combination of poloxamer gel components. In exemplary embodiments, the poloxamer gel is a combination of poloxamer 407 and poloxamer 188. The amount of poloxamer 407 in the compositions may be from 0.1% to 40%, 5% to 40%, 10% to 40%, 15% to 30%, 15% to 25% or 20% to 25% of the total weight of the composition. The amount of poloxamer 188 in the compositions may contribute from 0.1% to 40%, 5% to 40%, 10% to 40%, 15% to 30%, 15% to 25% or 20% to 25% towards the total weight of the composition.

In other embodiments, the compositions may further comprise other poloxamer gel components such as poloxamer 184, difunctional block copolymers possessing terminal hydroxyl groups and/or triblock copolymers. Examples of difunctional block copolymers possessing terminal hydroxyl groups are Pluronic P65, Pluronic P84, Pluronic P85, Pluronic F88, Pluronic P103, Pluronic 104 and Pluronic 105. Examples of triblock copolymers are Pluronic P108 and Pluronic P123. These poloxamer gels are to serve as examples of the additional poloxamer gels which may be included within the compositions and do not limit or prohibit the compositions from including other poloxamer gels.

The poloxamer gel components may have a size that is less than 0.42 mm. In some embodiments, the poloxamer gel components have a size ranging from 0.1 mm to 0.42 mm, 0.1 mm to 0.35 mm or 0.01 mm to 0.42 mm.

In some embodiments, the composition possesses a pH ranging from 4.5 to 8.0, ranging from 4.5 to 6.5, ranging from 5.0 to 6.0, or ranging from 5.5 to 6.0.

In other embodiments, the compositions may further comprise excipients. An excipient may be a moisturizer. The moisturizer may be either aloe vera, propylene glycol, polyethylene glycol, potassium salts and/or combinations thereof. The amount of each moisturizer in the compositions may range from 0.1% to 50%, 10% to 40%, 10% to 30%, 15% to 30%, 1% to 5%, 0.01% to 3% or 0.1% to 5%.

In some embodiments, the excipient may be a cleanser, such as xylitol. The amount of each cleanser in the compositions may range from 0.1% to 80%, 5% to 70%, 15% to 50%, 15% to 30%, 10% to 30% or 5% to 20%.

In other embodiments, the compositions also contain sodium chloride (NaCl). The presence of NaCl can increase the strength of the poloxamer gel; however, too much NaCl can cause the poloxamer gel to become too hard or strong, thus causing difficult application and removal. Poloxamer gel compositions that are too strong may also compromise the breathing of the subject. The addition of NaCl also affects the gelation temperature of the poloxamer gel. In embodiments where the compositions further include NaCl, the amount of NaCl may contribute from 0.01% to 50%, 5% to 40%, 10% to 30%, 10% to 20%, 5% to 20%, 0.01% to 2.0%, 1.0% to 2.0%, 1.0% to 1.5%, 0.01% to 1.0%, 0.01% to 0.1%, 0.1% to 0.5% or 0.5% to 1.0% towards the total weight of the composition.

In some embodiments, the compositions produce a poloxamer gel that possesses a gel strength between 25 s and 50 s. When the gel strength is less than 25 s the gel may not preserve its integrity and can erode rapidly. When the gel strength is greater than 50 s, the gel may become to too still or rigid and could cause discomfort. These gel strengths pertain to when the poloxamer gel compositions are exposed to temperatures around 34° C., such as those observed inside the nasal cavity. These gel strength parameters do not apply when the poloxamer gel compositions are exposed to room temperatures.

In other embodiments, the compositions do not possess a pharmaceutical agent such as, but not limited to, cell signaling molecules, antibiotics, antifungals, antivirals, anti-inflammatories, corticosteroids, drug-approved small molecules or other compounds used to alleviate or treat a disease or infection. In other embodiments, the compositions do not possess radioactive materials or biomarkers.

In some embodiments, the composition consists only of a poloxamer gel combination. In other embodiments, the composition consists only of a poloxamer gel combination and NaCl.

In other embodiments, the composition consists only of a poloxamer gel, wherein the poloxamer gel is a combination of poloxamer 407 and poloxamer 188. The amount of poloxamer 407 may contribute from 0.01% to 49.99% towards the total weight of the composition and the amount of poloxamer 188 may contribute from 49.99% to 0.01% towards the total weight of the composition.

In some embodiments, the composition consists only of a poloxamer gel and NaCl, wherein the poloxamer gel is a combination of poloxamer 407 and poloxamer 188. The amount of poloxamer 407 may contribute from 0.01% to 49.98% towards the total weight of the composition, the amount of poloxamer 188 may contribute from 49.98% to 0.01% towards the total weight of the composition and the amount of NaCl may contribute from 49.98% to 0.01% towards the total weight of the composition.

In some embodiments, the composition consists only of a poloxamer gel, NaCl, moisturizers and cleansers.

In other embodiments, the composition consists only of a poloxamer gel, NaCl and moisturizers.

In some embodiments, the composition consists only of a poloxamer gel, NaCl and cleansers.

In other embodiments, the composition is a liquid at temperatures ranging from 2° C. to 25° C., a soft gel at temperatures ranging from 25.5° to 28.9° C. and/or a solid at temperatures ranging from 30° C. to 36° C.

A poloxamer gel composition may be a solid at temperatures ranging from 30° C. to 36° C. when the viscosity of the composition is at least 10 times, or at least 100 times, or at least 1000 times the viscosity of the poloxamer gel composition at temperatures ranging from 25.5° to 28.9° C. or 2° C. to 25° C.

A poloxamer gel composition may be a solid at temperatures ranging from 30° C. to 36° C. when the viscosity of the composition is at least 10%, at least 20%, at least 30%, at least 40% or at least 50% higher when compared to the viscosity of the poloxamer gel composition at temperatures ranging from 30° C. to 36° C.

In some embodiments, the poloxamer gel composition is a solid at temperatures ranging from 30° C. to 36° C. and may possess a viscosity that is greater than 350 cP, greater than 500 cP, greater than 1,000 cP, greater than 200,000 cP, greater than 500,000 cP, greater than 1,000,000 cP or greater than 5,000,000 cP. In other embodiments, the viscosity of a solid poloxamer gel composition cannot be measured or determined by conventional methods such as through the use of a small sample adapter, a viscometer and a water bath.

A poloxamer gel composition may be a solid at temperatures ranging from 30° C. to 36° C. when the flow rate of the composition is at least 10%, at least 20%, at least 30%, at least 40% or at least 50% lower when compared to the flow rate of the poloxamer gel composition at temperatures ranging from 25.5° to 28.9° C. or 2° C. to 25° C.

A poloxamer gel composition may be a solid at temperatures ranging from 30° C. to 36° C. when the gel strength of the composition is at least 10%, at least 20%, at least 30%, at least 40% or at least 50% higher when compared to the strength of the poloxamer gel composition at temperatures ranging from 25.5° to 28.9° C. or 2° C. to 25° C.

A poloxamer gel composition may be a solid at temperatures ranging from 30° C. to 36° C. when the mechanical modulus of the composition is at least 10%, at least 20%, at least 30%, at least 40% or at least 50% higher when compared to the mechanical modulus of the poloxamer gel composition at temperatures ranging from 25.5° to 28.9° C. or 2° C. to 25° C.

A poloxamer gel composition may be a solid at temperatures ranging from 30° C. to 36° C. when the flexural modulus of the composition is at least 10%, at least 20%, at least 30%, at least 40% or at least 50% higher when compared to the flexural modulus of the poloxamer gel composition at temperatures ranging from 25.5° to 28.9° C. or 2° C. to 25° C.

A poloxamer gel composition may be a solid at temperatures ranging from 30° C. to 36° C. when the elastic modulus of the composition is at least 10%, at least 20%, at least 30%, at least 40% or at least 50% higher when compared to the elastic modulus of the poloxamer gel composition at temperatures ranging from 25.5° to 28.9° C. or 2° C. to 25° C.

A poloxamer gel composition may be a solid at temperatures ranging from 30° C. to 36° C. when the stiffness of the composition is at least 10%, at least 20%, at least 30%, at least 40% or at least 50% higher when compared to the stiffness of the poloxamer gel composition at temperatures ranging from 25.5° to 28.9° C. or 2° C. to 25° C.

A poloxamer gel composition may be a solid at temperatures ranging from 30° C. to 36° C. when the tensile strength of the composition is at least 10%, at least 20%, at least 30%, at least 40% or at least 50% higher when compared to tensile strength of the poloxamer gel composition at temperatures ranging from 25.5° to 28.9° C. or 2° C. to 25° C.

A poloxamer gel composition may be a soft gel at temperatures ranging from 25.5° to 28.9° C. when the viscosity of the composition is at least 10 times, or at least 100 times, or at least 1000 times lower than the viscosity of the poloxamer gel composition at temperatures ranging from 30° C. to 36° C.

A poloxamer gel composition may be a soft gel at temperatures ranging from 25.5° to 28.9° C. when the viscosity of the composition is at least 10%, at least 20%, at least 30%, at least 40% or at least 50% lower than the viscosity of the poloxamer gel composition at temperatures ranging from 30° C. to 36° C.

In some embodiments, the poloxamer gel composition may be a soft gel at temperatures ranging from 25.5° to 28.9° C. and possess a viscosity that may be less than about 10,000 cP, less than about 1,000 cP, less than about 300 cP, less than about 280 cP or less than 260 cP.

A poloxamer gel composition may be a soft gel at temperatures ranging from 25.5° to 28.9° C. when the flow rate of the composition is at least 10%, at least 20%, at least 30%, at least 40% or at least 50% higher when compared to the flow rate of the poloxamer gel composition at temperatures ranging from 30° C. to 36° C.

A poloxamer gel composition may be a soft gel at temperatures ranging from 25.5° to 28.9° C. when the gel strength of the composition is at least 10%, at least 20%, at least 30%, at least 40% or at least 50% lower when compared to the gel strength of the poloxamer gel composition at temperatures ranging from 30° C. to 36° C.

A poloxamer gel composition may be a soft gel at temperatures ranging from 25.5° to 28.9° C. when the mechanical modulus of the composition is at least 10%, at least 20%, at least 30%, at least 40% or at least 50% lower when compared to the viscosity of the poloxamer gel composition at temperatures ranging from 30° C. to 36° C.

A poloxamer gel composition may be a soft gel at temperatures ranging from 25.5° to 28.9° C. when the flexural modulus of the composition is at least 10%, at least 20%, at least 30%, at least 40% or at least 50% lower when compared to the flexural modulus of the poloxamer gel composition at temperatures ranging from 30° C. to 36° C.

A poloxamer gel composition may be a soft gel at temperatures ranging from 25.5° to 28.9° C. when the elastic modulus of the composition is at least 10%, at least 20%, at least 30%, at least 40% or at least 50% lower when compared to the elastic modulus of the poloxamer gel composition at temperatures ranging from 30° C. to 36° C.

A poloxamer gel composition may be a soft gel at temperatures ranging from 25.5° to 28.9° C. when the stiffness of the composition is at least 10%, at least 20%, at least 30%, at least 40% or at least 50% lower when compared to the stiffness of the poloxamer gel composition at temperatures ranging from 30° C. to 36° C.

A poloxamer gel composition may be a soft gel at temperatures ranging from 25.5° to 28.9° C. when the tensile strength of the composition is at least 10%, at least 20%, at least 30%, at least 40% or at least 50% lower when compared to the tensile strength of the poloxamer gel composition at temperatures ranging from 30° C. to 36° C.

A poloxamer gel composition may be a soft gel at temperatures ranging from 25.5° to 28.9° C. when the viscosity of the composition is at least 10 times, or at least 100 times, or at least 1000 times the viscosity of the poloxamer gel composition at temperatures ranging from 2° C. to 25° C.

A poloxamer gel composition may be a soft gel at temperatures ranging from 25.5° to 28.9° C. when the viscosity of the composition is at least 10%, at least 20%, at least 30%, at least 40% or at least 50% higher than the viscosity of the poloxamer gel composition at temperatures ranging from 2° C. to 25° C.

A poloxamer gel composition may be a soft gel at temperatures ranging from 25.5° to 28.9° C. when the flow rate of the composition is at least 10%, at least 20%, at least 30%, at least 40% or at least 50% lower when compared to the flow rate of the poloxamer gel composition at temperatures ranging from 2° C. to 25° C.

A poloxamer gel composition may be a soft gel at temperatures ranging from 25.5° to 28.9° C. when the gel strength of the composition is at least 10%, at least 20%, at least 30%, at least 40% or at least 50% higher when compared to the gel strength of the poloxamer gel composition at temperatures ranging from 2° C. to 25° C.

A poloxamer gel composition may be a soft gel at temperatures ranging from 25.5° to 28.9° C. when the mechanical modulus of the composition is at least 10%, at least 20%, at least 30%, at least 40% or at least 50% higher when compared to the mechanical modulus of the poloxamer gel composition at temperatures ranging from 2° C. to 25° C.

A poloxamer gel composition may be a soft gel at temperatures ranging from 25.5° to 28.9° C. when the flexural modulus of the composition is at least 10%, at least 20%, at least 30%, at least 40% or at least 50% higher when compared to the flexural modulus of the poloxamer gel composition at temperatures ranging from 2° C. to 25° C.

A poloxamer gel composition may be a soft gel at temperatures ranging from 25.5° to 28.9° C. when the elastic modulus of the composition is at least 10%, at least 20%, at least 30%, at least 40% or at least 50% higher when compared to the elastic modulus of the poloxamer gel composition at temperatures ranging from 2° C. to 25° C.

A poloxamer gel composition may be a soft gel at temperatures ranging from 25.5° to 28.9° C. when the stiffness of the composition is at least 10%, at least 20%, at least 30%, at least 40% or at least 50% higher when compared to the stiffness of the poloxamer gel composition at temperatures ranging from 2° C. to 25° C.

A poloxamer gel composition may be a soft gel at temperatures ranging from 25.5° to 28.9° C. when the tensile strength of the composition is at least 10%, at least 20%, at least 30%, at least 40% or at least 50% higher when compared to tensile strength of the poloxamer gel composition at temperatures ranging from 2° C. to 25° C.

A poloxamer gel composition may be a liquid at temperatures ranging from 2° C. to 25° C. when the viscosity of the composition is at least 10%, at least 20%, at least 30%, at least 40% or at least 50% lower than the viscosity of the poloxamer gel composition at temperatures ranging from 25.5° to 28.9° C.

A poloxamer gel composition may be a liquid at temperatures ranging from 2° C. to 25° C. when the viscosity of the composition is at least 10 times, or at least 100 times, or at least 1000 times lower than the viscosity of the poloxamer gel composition at temperatures ranging from 30° C. to 36° C.

A poloxamer gel composition may be a liquid at temperatures ranging from 2° C. to 25° C. when the viscosity of the composition is at least 10%, at least 20%, at least 30%, at least 40% or at least 50% lower than the viscosity of the poloxamer gel composition at temperatures ranging from 30° C. to 36° C.

In some embodiments, the compositions may further comprise water, preferably preserved water. The preserved water may comprise or consist of methylparaben, propylparaben and purified water. A list of exemplary preservatives that can be included in the compositions disclosed herein, and exemplary amounts, is provided below:

| Preservative | Conc. Range % w/v |
|---|---|
| Benzalkonium Chloride | 0.002-0.02 |
| Benzethonium Chloride | 0.01-0.02 |
| Benzoic Acid | 0.01-0.2 |
| Benzyl Alcohol | Up to 3 |
| Bronopol | 0.001-0.05 |
| Butylparaben | 0.006-0.4 |

-continued

| Preservative | Conc. Range % w/v |
|---|---|
| Cetrimide | 0.001-0.3 |
| Cetrimonium Bromide | 0.001-0.3 |
| Cetylpyridinium Bromide | 0.001-0.3 |
| Chlorhexidine | 0.002-0.01 |
| Chloroacetamide | up to 0.3 |
| Chlorobutanol | 0.5 |
| Chlorocresol | up to 0.2 |
| Chloroxylenol | 0.1-0.8 |
| Cresol | 0.15-0.3 |
| Dichlorophene | 0.001-1.00 |
| Domiphen Bromide | 0.001-1.00 |
| Ethylhexylglycerin | 0.5-1.0 |
| Ethylparaben | 0.001-1.00 |
| Ethylparaben Potassium | 0.001-1.00 |
| Ethylparaben Sodium | 0.001-1.00 |
| Hecachlorophene | 0.001-1.00 |
| Hexetidine | 0.1 |
| Imidurea | 0.03-0.5 |
| Methylparaben | 0.015-0.3 |
| Methylparaben Potassium | 0.001-1.00 |
| Methylparaben Sodium | 0.001-1.00 |
| Phenol | 0.5-1.0 |
| Phenoxyethanol | 0.5-1.0 |
| Phenylethyl Alcohol | 0.25-0.5 |
| Phenylmercuric Acetate | 0.001-0.002 |
| Phenylmercuric Borate | 0.002-0.004 |
| Phenylmercuric Nitrate | 0.001-0.02 |
| Phospholipid (PTC) | 0.001-1.00 |
| Piroctone Olamine | 0.001-1.00 |
| Polyaminopropylbiguanide | up to 0.3 |
| Polyhexanide | 0.02 |
| Polyhexymethylbiguanide | up to 0.3 |
| Potassium Benzoate | 0.03-0.08 |
| Potassium Sorbate | 0.1-0.2 |
| Propylparaben | 0.02 |
| Propylparaben Potassium | 0.001-1.00 |
| Propylparaben Sodium | 0.001-1.00 |
| Sodium Benzoate | 0.02-0.5 |
| Sodium Propionate | 0.001-1.00 |
| Sorbic Acid | 0.05-0.2 |
| Thimerosal | 0.1 |
| Trichlorcarban | 0.001-1.00 |
| Triclocarban | 0.3 |

The preserved water may include purified water and any of (or any combination of) the above listing of preservatives.

In other embodiments, the composition may comprises a poloxamer gel, wherein the poloxamer gel is a combination of poloxamer 407 and poloxamer 188; wherein the composition further comprises preserved water; wherein the composition is a gel at temperatures ranging from 25.5° C. to 28.9° C. and a solid at temperatures ranging from 30° C. to 36° C., and wherein the composition is prepared by sieving poloxamer 407 and poloxamer 188 to a particle size not exceeding 0.42 mm. In embodiments where the composition further comprises other poloxamers besides 407 and 188, those poloxamers may also be sieved to a particle size not exceeding 0.42 mm.

In some embodiments, the composition comprises a poloxamer gel, wherein the poloxamer gel is a combination of poloxamer 407 and poloxamer 188, wherein the composition is prepared by any of the methods disclosed herein. Compositions further comprising other poloxamers besides 407 and 188 may also be prepared by any of the methods disclosed herein.

The poloxamer gels described herein may also possess a syrup consistency at temperatures ranging from 20° C. to 25° C. As used herein, a "syrup consistency" refers to a poloxamer gel solution possessing a viscosity within the range of 150 cps to 70,000 cps.

Any of the compositions disclosed within the present disclosure may also be prepared by any of the methods disclosed herein.

Another aspect of the present disclosure is a method for the preparation of the poloxamer gel compositions.

In some embodiments, the method for preparing the poloxamer gel compositions comprises adding preserved water into a reaction vessel, passing the poloxamer gel components through a sieve mesh before adding them to the reaction vessel, adding the sieved poloxamer gel components to the reaction vessel, adding cold preserved water to the reaction vessel, stirring the poloxamer gel solution at room temperature and storing the solution at a temperature between 0° C. to 4° C.

In other embodiments, the method for preparing the poloxamer gel compositions may further comprise storing the solution at a temperature between 0° C. to 4° C. between 12 to 24 hours. In some embodiments, cold preserved water is added to the solution after storing the solution at a temperature between 0° C. to 4° C. for 12 to 24 hours. The solution may further be stirred and stored at a temperature between 0° C. to 4° C. for 2 to 3 hours after the addition of the cold preserved water. The solution may become a clear gel of low to medium viscosity once stored at temperatures between 0° C. to 4° C. The solution may also become a solid when exposed to room temperatures after storing at temperatures between 0° C. to 4° C.

In some embodiments, the method for preparing the poloxamer gel compositions may further comprise adjusting the pH of the solution to a pH between 4.5 and 8.0 through the addition of an acid or base to the solution.

In other embodiments, the method for preparing the poloxamer gel compositions may further comprise adding 10% more of the poloxamer gel components to the solution. The addition of more poloxamer gel components to the solution can help achieve the weight percentages that the poloxamer gel components can contribute to the total weight of the solution by compensating for any loss of poloxamer gel components during the preparation process.

In some embodiments, the sieve mesh that the poloxamer gel components pass through may be a 40-mesh sieve. The use of a 40-mesh sieve allows the poloxamer gel components to achieve a size that is at most 0.42 mm. The poloxamer gel components may also be further sieved to achieve sizes that range from 0.1 mm to 0.42 mm, 0.1 mm to 0.35 mm, or 0.01 mm to 0.42 mm. In embodiments, the mean (D50) size of the poloxamer gel components may range from 0.05 mm, 0.1 mm, or 0.15 mm to 0.25 mm, 0.35 mm, 0.42 mm, 0.5 mm, 0.7 mm, or 1 mm. An advantage of reducing the size of the poloxamer gel components to those presented above is that the poloxamer gel components are more readily hydrated by the preserved water during the mixing and storing steps. When the poloxamer gel components reach a size above 0.42 mm, they take longer to hydrate and the gelling of the solution is slowed. In some cases, the complete hydration of the poloxamer gel components possessing sizes over 0.42 mm could take more than 2 days.

In other embodiments, the method for preparing the poloxamer gel compositions may further comprise adding NaCl to the poloxamer gel solution after storing at temperatures between 0° C. to 4° C. The method may further comprise adding NaCl to a separate reaction vessel and adding cold preserved water to the reaction vessel until the NaCl is completely dissolved in the preserved water.

In some embodiments, the method for preparing the poloxamer gel compositions may further comprise adding the stored poloxamer gel solution to the solution of NaCl until a final volume is achieved. The NaCl solution may be mixed during the addition of the stored poloxamer gel solution. The combined solution of NaCl and poloxamer gel components may be stored at room temperature in a light-resistant reaction vessel.

Another aspect of the present disclosure is a method for treating nosebleeds comprising administering to a subject in need thereof a poloxamer gel composition described herein. In preferred embodiments, the poloxamer gel composition is administered to a subject in need thereof via the nasal cavity. The administration of the poloxamer gel composition may be through physical application with either a nasal dropper, a nasal sprayer, a nasal swab, a nasal tube, a respule or a nasal applicator stick.

In other embodiments, the method further comprises administering a poloxamer gel routinely to a subject in need thereof. The poloxamer gel may be administered once a day, twice a day, three times a day, four times a day or more than four times a day if needed by the subject in need thereof.

In some embodiments, the method for treating nosebleeds may further comprise reducing number of nosebleeds per day in a subject in need thereof.

In other embodiments, the method for treating nosebleeds may further comprise reducing the severity of nose bleeds in a subject in need thereof. The severity of a nose bleed can be quantified by measuring the volume of blood lost during the nosebleed or measuring the duration of the nosebleed.

In one embodiment, the composition comprises a poloxamer gel. The poloxamer gel may be a combination of poloxamer 407 and poloxamer 188. The composition may further comprise preserved water. The composition may be free of pharmaceutical agents and radioactive compounds. The composition may be formed from poloxamer gel components having a small size, such as a mean size of at most 0.5 mm. The composition may be a gel at temperatures ranging from 25.5° C. to 28.9° C. The composition may be a solid at temperatures ranging from 30° C. to 36° C. The composition, once applied to a nasal cavity of a subject in need thereof, may reduce the number of nosebleeds per day in the subject in need thereof. The composition, once applied to a nasal cavity of a subject in need thereof, may reduce the severity of nose bleeds in the subject in need thereof.

EXAMPLES

Example 1: Poloxamer Gel Formulations and their Gelation Properties

List of Components in Poloxamer Gel Formulations:

Poloxamer 407

Poloxamer 188

NaCl

The pH ranges of the formulations recited within this Example range from 4.5 to 6.5.

The gelation and physical properties of various poloxamer gel formulations are depicted in Table 1.

TABLE 1

Poloxamer gel formulations and their gelation properties at various temperatures

| Formulation | Temperature: 2° C.-7.7° C. | Temperature: 20° C.-25° C. | Temperature: 25.5° C.-29° C | Temperature: 30° C.-36° C. | Observations |
|---|---|---|---|---|---|
| Poloxamer 407 15%/Poloxamer 188 15% | Liquid | Liquid | Soft Gel | Soft Gel | Very fluid, never fully solidified even at higher temperatures |
| Poloxamer 407 15%/Poloxamer 188 17%/NaCl 0.9% | Liquid | Liquid | Soft Gel | Solid | Performed best and appropriately at all temperatures |
| Poloxamer 407 15%/Poloxamer 188 20% | Liquid | Liquid | Solid | Solid | Extremely thick, difficult to work with. |
| Poloxamer 407 20%/Poloxamer 188 10% | Liquid | Liquid | Solid | Solid | Extremely thick, difficult to work with. |
| Poloxamer 407 20%/Poloxamer 188 15% Gel | Liquid | Very Think Liquid | Solid | Solid | Nearly impossible to work with; most difficult to form a complete, hydrated gel. Almost solid from very start. |

Example 2: Method of Forming a Poloxamer Gel Composition

The poloxamer gel formed from the following exemplary method possesses the composition described in Table 2.

TABLE 2

Exemplary poloxamer gel composition

| FORMULA NAME | |
|---|---|
| POLOXAMER 407 15%/POLOXAMER 188 23%/BENZALKONIUM CHLORIDE (1:10 DILUTION) GEL | |
| BATCH YIELD | |
| 400 ML | |
| CHEMICAL | THEO-RETICAL |
| POLOXAMER 188 NF | 720 GM |
| POLOXAMER 407 NF | 1440 GM |
| STERILE WATER FOR IRRIGATION, USP LIQUID | 253.2 GM |
| SODIUM CHLORIDE USP POWDER | 3.6 GM |
| BENZALKONIUM CHLORIDE 1:10 DILUTION AQUEOUS SOLUTION | 1.64 GM |

The formula used to create the Benzalkonium Chloride 1:10 Dilution Aqueous Solution is provided in Table 3 below.

TABLE 3

Benzalkonium Chloride 1:10 Dilution

| FORMULA NAME | |
|---|---|
| BENZALKONIUM CHLORIDE 1:10 DILUTION AQUEOUS SOLUTION | |
| BATCH YIELD | |
| 10 GM | |
| CHEMICAL | THEO-RETICAL |
| BENZALKONIUM CHLORIDE SOLUTION NF 50% SOLUTION (PCCA-brand) | 1 GM |
| STERILE WATER FOR IRRIGATION, USP LIQUID | 9 GM |

Method for Preparing the Exemplary Poloxamer Gel Composition:

To overcome any potential loss of components due to residue formation in the mixing device, 10% more of each component in the exemplary poloxamer gel composition formula above may be added. (e.g. batch quantity made will be 100 mL>10% extra>batch total YIELD will be for 110 mL).

The appropriate amount of the composition's powder components (i.e., POLOXAMER 188 NF, POLOXAMER 407 NF and SODIUM CHLORIDE USP POWDER) were first weighed out using any weight scale commonly employed in the art. Poloxamer 188 and Poloxamer 407 were then added to a tared beaker. Cold (refrigerated) sterile water was added to the beaker until 90% of the composition's final weight was achieved. The Benzalkonium Chloride 1:10 dilution solution was then added to the beaker. The composition in the beaker was then mixed thoroughly on a hot plate. During this mixing, Sodium Chloride was added to the beaker and the composition was allowed to continue mixing on hot plate until a homogenous mixture formed. Once the composition was mixed thoroughly, sterile water was added until the composition achieved its final weight. After achieving the final weight, the composition was refrigerated for 12-24 hours until all of the granules were thoroughly wet and the composition became a clear solution. The composition was then transferred to a labeled, light-resistant vial and stored in the refrigerator.

Method for Preparing the Benzalkonium Chloride 1:10 Dilution:

To overcome any potential loss of components due to residue formation in the mixing device, 10% more of each component in the Benzalkonium Chloride 1:10 dilution formula above may be added. (e.g. batch quantity made will be 100 mL>10% extra>batch total YIELD will be for 110 mL).

Using a syringe, the amount of Benzalkonium Chloride Solution NF 50% Solution was transferred into a tared beaker. Once the appropriate amount of Benzalkonium Chloride Solution NF 50% Solution was added, sterile water was added to the beaker until the final weight of the Benzalkonium Chloride 1:10 dilution was achieved. The solution was then stirred until uniform. Once the solution obtained a uniform mixing, it was stored in a labeled, light-resistant vial at room temperature.

What is claimed is:

1. A method for treating nosebleeds in a subject in need thereof comprising administering a poloxamer gel composition, wherein the poloxamer gel composition comprises poloxamer 407 and poloxamer 188, wherein the amount of poloxamer 407 contributes 0.1% to 50% towards the total weight of the composition and the amount of poloxamer 188 contributes 0.1% to 50% towards the total weight of the composition;
 wherein the poloxamer gel composition further comprises preserved water;
 wherein the poloxamer gel composition is a solid at temperatures ranging from 30° C. to 36° C.;
 wherein the composition is administered into the nasal cavity of the subject and wherein the method further comprises reducing the number of nosebleeds per day in the subject in need thereof.

2. The method of claim 1, wherein the composition further comprises NaCl in an amount that contributes 0.1% to 50% towards the overall weight of the composition.

3. The method of claim 1, wherein the composition is administered once or twice a day.

4. The method of claim 1, wherein the method further comprises reducing the severity of nose bleeds in the subject in need thereof.

5. The method of claim 1, wherein the composition does not contain pharmaceutical agents and radioactive compounds.

6. The method of claim 1, wherein the composition comprises an amount of poloxamer 407 that contributes 0.1% to 40% towards the total weight of the composition and an amount of poloxamer 188 that contributes 0.1% to 40% towards the total weight of the composition.

7. The method of claim 2, wherein the amount of poloxamer 407 contributes 10% to 20% towards the total weight of the composition and the amount of poloxamer 188 contributes 10% to 20% towards the total weight of the composition.

8. The method of claim 2, wherein NaCl is present in an amount that contributes 0.5% to 2.0% towards the total weight of the composition.

9. The method of claim 1, wherein the composition is a gel at temperatures ranging from 25.5° C. to 28.9° C. and a solid at temperatures ranging from 30° C. to 36° C.

10. The method of claim 1, wherein the composition further comprises an excipient selected from the group consisting of moisturizers, cleansers, and a combination thereof.

11. The method of claim 10, wherein the moisturizers contribute 0.1% to 50% towards the total weight of the composition and the cleansers contribute 0.1% to 80% towards the total weight of the composition.

12. The method of claim 11, wherein the moisturizers are selected from the group consisting of aloe vera, propylene glycol, polyethylene glycol, potassium salts, and combinations thereof, and wherein the cleanser is xylitol.

13. The method of claim 1, wherein the composition is formed from poloxamer gel components having a mean size of at most 0.5 mm.

14. The method of claim 1, wherein the composition comprises:

10-25 wt % of poloxamer 407;

10-25 wt % of poloxamer 188; and 0.6-1.1 wt % NaCl.

15. The method of claim 1, wherein the poloxamer gel composition possesses a pH between 4.5 and 6.5.

* * * * *